United States Patent
Ishii et al.

(10) Patent No.: US 6,706,915 B2
(45) Date of Patent: Mar. 16, 2004

(54) PROCESS FOR PRODUCING ORGANIC SULFUR ACIDS OR SALTS THEREOF

(75) Inventors: Yasutaka Ishii, Takatsuki (JP); Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 180 days.

(21) Appl. No.: 09/959,648

(22) PCT Filed: Feb. 27, 2001

(86) PCT No.: PCT/JP01/01462

§ 371 (c)(1),
(2), (4) Date: Nov. 2, 2001

(87) PCT Pub. No.: WO01/64629

PCT Pub. Date: Jul. 9, 2001

(65) Prior Publication Data

US 2002/0161255 A1 Oct. 31, 2002

(30) Foreign Application Priority Data

Mar. 2, 2000 (JP) ........................................ 2000-058055

(51) Int. Cl.$^7$ ................................................. C07G 1/00
(52) U.S. Cl. ........................................................ 562/30
(58) Field of Search ........................................... 562/30

(56) References Cited

U.S. PATENT DOCUMENTS 3,956,371 A    5/1976    Bjellqvist et al.

FOREIGN PATENT DOCUMENTS

GB    1052484    12/1966
JP    51-63162   6/1976

OTHER PUBLICATIONS

S Fumasoni et al. "Sulfonation of paraffins in presence of metallic ions", Rass Chim., 1985 pp. 179–184.

S Fumasoni et al. "Sulfoxidation of paraffin hydrocarbons in the presence of heavy metal ions", Nuova Chim. 1972, pp. 33–37.

Primary Examiner—Paul J. Killos
(74) Attorney, Agent, or Firm—Birch, Stewart, Kolasch & Birch, LLP

(57) ABSTRACT

A process for producing organic sulfur acid or a salt thereof of the present invention allows an organic substrate to react with a sulfur oxide in the presence of a metallic compound catalyst and in the absence of N-hydroxy and N-oxo cyclic imide compounds and thereby yields a corresponding organic sulfur acid or a salt thereof. Such organic substrates include, for example, (a) homocyclic or heterocyclic compounds having a methylene group, (b) compounds having a methine carbon atom, (c) compounds having a methyl group or methylene group at the adjacent position to an unsaturated bond, (d) non-aromatic heterocyclic compounds having a carbon-hydrogen bond at the adjacent position to a hetero atom, and (e) straight-chain alkanes. The sulfur oxide includes, for example, sulfur dioxide. This production process can efficiently produce an organic sulfur acid or a salt thereof under mild conditions.

5 Claims, No Drawings

PROCESS FOR PRODUCING ORGANIC SULFUR ACIDS OR SALTS THEREOF

This application is the national phase under 35 U.S.C. §371 of PCT International Application No. PCT/JP01/01462 which has an International filing date of Feb. 27, 2001, which designated the United States of America.

TECHNICAL FIELD

The present invention relates to a process for producing organic sulfur acids or salts thereof which are useful, for example, as materials for pharmaceuticals, agrochemicals and dyes or as detergents.

BACKGROUND ART

A variety of processes are known for producing organic sulfur acids or salts thereof. For example, such processes for producing a sulfonic acid include a process of oxidizing a thiol or disulfide with an oxidizing agent, a process of allowing an aromatic hydrocarbon to react with anhydrous $SO_3$-pyridine or chlorosulfuric acid by the use of a Friedel-Crafts reaction, and a process of synthetically obtaining a sulfonic acid by subjecting an unsaturated compound to free-radical addition. These processes, however, require extreme reaction conditions or inevitably produce large amounts of by-products. Separately, few processes for directly and efficiently sulfonating non-aromatic hydrocarbons have been known.

The Chemical Society of Japan, Spring Conference Proceedings (1999) reports on a sulfonation reaction of a hydrocarbon with sulfur dioxide and oxygen by catalysis of N-hydroxyphthalimide. This process can yield a corresponding sulfonic acid from a hydrocarbon such as adamantane through one step. However, demands have been made on a process for further efficiently producing sulfonic acids and other organic sulfur acids or salts thereof at a lower cost.

DISCLOSURE OF INVENTION

Accordingly, an object of the present invention is to provide a process for efficiently producing an organic sulfur acid or a salt thereof under mild conditions.

Another object of the present invention is to provide a process for directly and efficiently producing a corresponding sulfur acid or a salt thereof from a non-aromatic hydrocarbon.

After intensive investigations to achieve the above objects, the present inventors have found that, by using a metallic compound as a catalyst, a corresponding organic sulfur acid or a salt thereof can efficiently be obtained from an organic substrate and a sulfur oxide even in the absence of N-hydroxy and N-oxo cyclic imide compounds. The present invention has been accomplished based on these findings.

Specifically, the present invention provides a process for producing an organic sulfur acid or a salt thereof. The process includes the step of allowing an organic substrate to react with a sulfur oxide in the presence of a metallic compound catalyst and in the absence of N-hydroxy and N-oxo cyclic imide compounds to thereby yield a corresponding organic sulfur acid or a salt thereof. The sulfur oxide includes, for example, sulfur dioxide. Such organic substrates include, for example, (a) homocyclic or heterocyclic compounds each having a methylene group, (b) compounds each having a methine carbon atom, (c) compounds each having a methyl group or methylene group at the adjacent position to an unsaturated bond, (d) non-aromatic heterocyclic compounds each having a carbon-hydrogen bond at the adjacent position to a hetero atom, and (e) straight-chain alkanes.

The term "N-hydroxy and N-oxo cyclic imide compounds" specifically means compounds represented by following Formula (1):

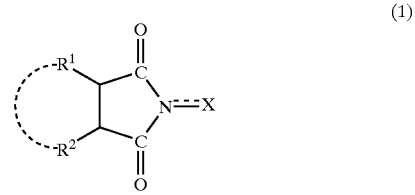

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group or an acyl group, where $R^1$ and $R^2$ may be combined to form a double bond or an aromatic or non-aromatic ring; X is an oxygen atom or a hydroxyl group, where one or two of N-substituted cyclic imido group indicated in the formula (1) may be further bonded to the aforementioned $R^1$, $R^2$ or to the double bond or aromatic or non-aromatic ring formed together by $R^1$ and $R^2$.

BEST MODE FOR CARRYING OUT THE INVENTION

[Organic Substrate]

The substrates for use in the invention are not specifically limited and include a wide variety of saturated or unsaturated compounds. Such compounds include, but are not limited to, hydrocarbons (aliphatic hydrocarbons, alicyclic hydrocarbons and aromatic hydrocarbons), heterocyclic compounds, alcohols, ethers, esters, ketones and aldehydes. Each of these substrates can be used alone or in combination.

Preferred substrates include, but are not limited to, (a) homocyclic or heterocyclic compounds each having a methylene group, (b) compounds each having a methine carbon atom, (c) compounds each having a methyl group or a methylene group at the adjacent position to an unsaturated bond, (d) non-aromatic heterocyclic compounds each having a carbon-hydrogen bond at the adjacent position to a hetero atom, and (e) straight-chain alkanes. In these compounds, a sulfur acid group such as a sulfonic acid group or sulfinic acid group is introduced into the methylene group, methine carbon atom, methyl group or methylene group, carbon atom at the adjacent position to the hetero atom, and carbon atom constituting the straight-chain alkane, respectively.

Of the compounds (a), homocyclic compounds (a1) having a methylene group include, but are not limited to, cycloalkanes (e.g., cyclopropane, cyclobutane, cyclopentane, cyclohexane, methylcyclohexane, 1,2-diethylcyclohexane, isopropylcyclohexane, cycloheptane, cyclooctane, methylcyclooctane, cyclononane, cyclodecane, cyclododecane, cyclotridecane, cyclotetradecane, cyclopentadecane, cyclohexadecane, cyclooctadecane, cyclononadecane, and other $C_3$–$C_{30}$ cycloalkanes), cycloalkenes (e.g., cyclopropene, cyclobutene, cyclopentene, cyclohexene, 1-methyl-1-cyclohexene, cycloheptene, cyclooctene, cyclononene, cyclodecene, cyclododecene, and other $C_3$–$C_{30}$ cycloalkenes), cycloalkadienes (e.g., cyclopentadiene, cyclohexadiene, cycloheptadiene, cyclooctadiene, cyclodecadiene, cyclododecadiene, and other $C_5$–$C_{30}$ cycloalkadienes), cycloalkatrienes, cycloalkatetraenes, and condensed polycyclic aromatic hydrocarbons each having a 5- to 8-membered non-aromatic ring condensed therewith.

Of the compounds (a), heterocyclic compounds (a2) each having a methylene group include, for example, 5- or 6-membered cyclic compounds having a hetero atom selected from nitrogen, oxygen and sulfur atoms, or condensed heterocyclic compounds having an aromatic ring and a 5- or 6-membered ring having a hetero atom condensed to the aromatic ring. Examples of such heterocyclic compounds (a2) are dihydrofuran, tetrahydrofuran, pyran, dihydropyran, tetrahydropyran, piperidine, piperazine, pyrrolidine and xanthene. In the compounds (a), a sulfur acid group is introduced into the methylene group constituting a non-aromatic ring.

The compounds (b) each having a methine carbon atom (a methylidyne group) include, for example, (b1) chain hydrocarbons each having a tertiary carbon atom, (b2) bridged cyclic compounds and (b3) non-aromatic cyclic compounds each having a hydrocarbon group bonded to its ring.

The chain hydrocarbons (b1) each having a tertiary carbon atom include, but are not limited to, isobutane, isopentane, isohexane, 3-methylpentane, 2,3-dimethylbutane, 2-methylhexane, 3-methylhexane, 2,3-dimethylpentane, 2,4-dimethylpentane, 2,3,4-trimethylpentane, 3-ethylpentane, 2,3-dimethylhexane, 2,4-dimethylhexane, 3,4-dimethylhexane, 2,5-dimethylhexane, 2-propylhexane, 2-methylheptane, 4-methylheptane, 2-ethylheptane, 3-ethylheptane, 2,6-dimethylheptane, 2-methyloctane, 3-methyloctane, 2,7-dimethyloctane, 2-methylnonane, and other aliphatic hydrocarbons each having from about 4 to about 20 (preferably from about 4 to about 10) carbon atoms. In the compounds (b1), a sulfur acid radical is introduced into the tertiary carbon atom.

The bridged cyclic compounds (b2) include, but are not limited to, decalin, bicyclo[2.2.0]hexane, bicyclo[2.2.2]octane, bicyclo[3.2.1]octane, bicyclo[4.3.2]undecane, thujone, carane, pinane, pinene, bornane, bornylene, norbornane, norbornene, camphor, camphoric acid, camphene, tricyclene, tricyclo[4.3.1.1$^{2,5}$]undecane, tricyclo[5.2.1.0$^{3,8}$]decane, exotricyclo[5.2.1.0$^{2,6}$]decane, endotricyclo[5.2.1.0$^{2,6}$]decane, endotricyclo[5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, 2-adamantanone, tetracyclo[4.4.0.1$^{2,5}$.1$^{7,10}$]dodecane, perhydroanthracene, perhydroacenaphthene, perhydrophenanthrene, perhydrophenalene, perhydroindene, quinuclidine, and other bicyclic, tricyclic or tetracyclic bridged hydrocarbons or bridged heterocyclic compounds and derivatives of these compounds. These bridged cyclic compounds (b2) each have a methine carbon atom at a bridgehead position (corresponding to a junction position when two rings commonly possess two atoms), and a sulfur acid group is introduced into the methine carbon atom.

The non-aromatic cyclic compounds (b3) each having a hydrocarbon group bonded to its ring include, for example, 1-methylcyclopentane, 1-methylcyclohexane, limonene, menthene, menthol, carvomenthone, menthone, and other alicyclic hydrocarbons each having from about 3 to about 15 members and having a hydrocarbon group (e.g., an alkyl group) each having from about 1 to about 20 (preferably from about 1 to about 10) carbon atoms and being bonded to its ring, and derivatives of these compounds. In these compounds (b3), a sulfur acid group is introduced into a methine carbon atom at the bonding site between the constitutive ring and the hydrocarbon group.

The compounds (c) each having a methyl group or a methylene group at the adjacent position to an unsaturated bond include (c1) organic compounds each having a methyl group or a methylene group at the adjacent position to a non-aromatic carbon-carbon double bond and/or triple bond, (c2) compounds each having a methyl group or a methylene group at the adjacent position to an aromatic ring, and (c3) compounds each having a methyl group or a methylene group at the adjacent position to a carbonyl group.

The compounds (c1) include, but are not limited to, unsaturated chain hydrocarbons each having from about 3 to about 12 carbon atoms, such as propylene, 1-butene, 2-butene, butadiene, 1-pentene, 2-pentene, isoprene, 1-hexene, 2-hexene, 1,5-hexadiene, 2,3-dimethyl-2-butene, 3-hexene, 1-heptene, 2-heptene, 1,6-heptadiene, 1-octene, 2-octene, 3-octene, 1,7-octadiene, 2,6-octadiene, 2-methyl-2-butene, 1-nonene, 2-nonene, decene, decadiene, dodecene, dodecadiene, dodecatriene, undecene, undecadiene and undecatriene. In these compounds (c1), a sulfur acid group is introduced into, for example, a carbon atom at an allylic position.

The compounds (c2) include, but are not limited to, aromatic hydrocarbons each having an alkyl group (e.g., toluene, xylene, mesitylene, durene, ethylbenzene, propylbenzene, cumene, methylethylbenzene, methylnaphthalene, dimethylnaphthalene, methylanthracene, dimethylanthracene, trimethylanthracene, dibenzyl, diphenylmethane and triphenylethane); and heterocyclic compounds each having an alkyl group [e.g., methylfuran, methylchroman, methylpyridine (picoline), dimethylpyridine (lutidine), trimethylpyridine (collidine), ethylpyridine, methylquinoline, methylindole, indan, indene, tetralin and fluorene]. In these compounds (c2), a sulfur acid group is introduced into a so-called benzylic position.

The compounds (c3) include, for example, aldehydes, ketones, carboxylic acids and derivatives thereof. Such aldehydes include, but are not limited to, aliphatic aldehydes (e.g., acetaldehyde, propionaldehyde, butyraldehyde, isobutyraldehyde, pentyl aldehyde, hexyl aldehyde, heptyl aldehyde, octyl aldehyde, nonyl aldehyde, decyl aldehyde, and other $C_2$–$C_{12}$ alkyl monoaldehydes, malonaldehyde, succinaldehyde, adipaldehyde, sebacaldehyde, and other aliphatic polyaldehydes), alicyclic aldehydes (e.g., formylcyclohexane and cycloneral), and heterocyclic aldehydes.

The ketones include, but are not limited to, aliphatic ketones (e.g., acetone, methyl ethyl ketone, methyl isopropyl ketone, methyl isobutyl ketone, methyl t-butyl ketone, 2-pentanone, 3-pentanone, 2-hexanone, 3-hexanone, 2-heptanone, 3-heptanone, 4-heptanone, 2-octanone, 3-octanone, 4-octanone, 2-nonanone and 2-decanone), cyclic ketones (e.g., cyclopentanone, cyclohexanone, methylcyclohexanone, dimethylcyclohexanone, cycloheptanone, isophorone, cyclooctanone, cyclononanone, cyclodecanone, cyclohexadione, cyclooctadione, and other non-aromatic cyclic mono- or poly-ketones; and α-tetralone, β-tetralone, indanone, and other cyclic ketones each having an aromatic ring), bridged cyclic ketones (e.g., adamantanone, methyladamantanone and dimethyladamantanone), aromatic ketones (e.g., acetophenone and propiophenone) and heterocyclic ketones (e.g., inden-1-one, and fluoren-9-one)

The carboxylic acids and derivatives thereof include, for example, aliphatic dicarboxylic acids and derivatives thereof (e.g., malonic acid and its esters, succinic acid and its esters, glutaric acid and its esters). In the compounds (c3), a sulfur acid group is introduced into, for example, a so-called active methylene group or methyl group.

In the non-aromatic heterocyclic compounds (d) each having a carbon-hydrogen bond at the adjacent position to a hetero atom, non-aromatic heterocyclic rings include, but are not limited to, 3- to 20-membered (preferably 5- to 12-membered, and more preferably 5- or 6-membered) heterocyclic rings each having at least one hetero atom selected from nitrogen, oxygen and sulfur atoms. To each of the heterocyclic rings, one or more benzene rings, cyclohexane rings, pyridine rings or other aromatic or non-aromatic rings may be condensed. Examples of the heterocyclic rings include dihydrofuran, tetrahydrofuran, pyran, dihydropyran, tetrahydropyran, pyrrolidine, piperidine, piperazine, morpholine, indoline, chroman and isochroman.

The straight-chain alkanes (e) include, but are not limited to, methane, ethane, propane, butane, pentane, hexane, heptane, octane, nonane, decane, dodecane, tetradecane, hexadecane, and other straight-chain alkanes each having from about 1 to about 30 carbon atoms, and preferably from about 1 to about 20 carbon atoms.

These substrates may have an appropriate functional group substituted thereto. Such functional groups include, for example, halogen atoms, alkyl groups, alkenyl groups, alkynyl groups, cycloalkyl groups, aryl groups, aralkyl groups, acyl groups, hydroxyl group, alkoxy groups, acyloxy groups, mercapto group, carboxyl group, alkoxycarbonyl groups, amino group, N-substituted amino groups, carbamoyl group, N-substituted carbamoyl groups, nitro group, cyano group, sulfonyl group, sulfinyl group, phosphino group, heterocyclic groups and oxo group.

[Sulfur Oxide and Oxygen]

The sulfur oxides can be shown by the formula: $S_xO_y$ wherein x is an integer of 1 or 2; and y is an integer of 1 to 7. In the compounds of the formula, y is usually an integer of 1 to 4 when x is 1, and y is generally 3 or 7 when x is 2.

Such sulfur oxides include, but are not limited to, SO, $S_2O_3$, $SO_2$, $SO_3$, $S_2O_7$, and $SO_4$. Each of these sulfur oxides can be used alone or in combination. A preferred sulfur oxide includes sulfur dioxide ($SO_2$). The sulfur oxide can be used in combination with oxygen. For example, the combination use of sulfur dioxide ($SO_2$) with oxygen can yield a corresponding sulfonic acid in a high yield. The oxygen may be either pure oxygen or oxygen diluted with an inert gas such as carbon dioxide, nitrogen, helium or argon gas. The oxygen source can also be air. As sulfur trioxide, fuming sulfuric acid containing sulfur trioxide can be employed.

The amount of the sulfur oxide can be selected according to the amount of sulfur acid groups (e.g., sulfonic acid groups or sulfinic acid groups) introduced into the organic substrate, and is, for example, from about 1 to about 50 moles, and preferably from about 1.5 to about 30 moles relative to 1 mole of the substrate. The reaction can be performed in an atmosphere of the sulfur oxide in large excess. When the sulfur oxide such as sulfur dioxide ($SO_2$) is used in combination with oxygen, the molar ratio of the sulfur oxide to oxygen is such that the former/the latter is from about 1/99 to about 99/1, and preferably from about 10/90 to about 90/10, and more preferably from about 20/80 to about 80/20.

[Catalyst]

According to the process of the present invention, a metallic compound is used as a catalyst. Each of such metallic compounds can be used alone or in combination.

Metallic elements for constituting the metallic compounds are not specifically limited and can be any of metallic elements of the Groups 1 to 15 of the Periodic Table of Elements. The term "metallic element" as used herein also includes boron, B. Examples of the metallic elements include, of the Periodic Table of Elements, Group 1 elements (e.g., Li, Na and K), Group 2 elements (e.g., Mg, Ca, Sr and Ba), Groups 3 elements (e.g., Sc, lanthanoid elements and actinoid elements), Group 4 elements (e.g., Ti, Zr and Hf), Group 5 elements (e.g., V), Group 6 elements (e.g., Cr, Mo and W), Group 7 elements (e.g., Mn), Group 8 elements (e.g., Fe and Ru), Group 9 elements (e.g., Co and Rh), Group 10 elements (e.g., Ni, Pd and Pt), Group 11 elements (e.g., Cu), Group 12 elements (e.g., Zn), Groups 13 elements (e.g., B, Al and In), Group 14 elements (e.g., Sn and Pb) and Group 15 elements (e.g., Sb and Bi). Preferred metallic elements include transition metal elements (elements of Groups 3 to 12 of the Periodic Table of Elements). Among them, elements of the Groups 5 to 11 of the Periodic Table of Elements are more preferred, of which vanadium and other Group 5 elements are typically preferred. The valences of the metallic elements are not specifically limited and may be about 1 to 6, and are from about 3 to about 5 in many cases.

The metallic compounds include, but are not limited to, elementary substances, hydroxides, oxides (including complex oxides), halides (fluorides, chlorides, bromides and iodides), salts of oxoacids (e.g., nitrates, sulfates, phosphates, borates, and carbonates), oxoacids, isopolyacids, heteropolyacids, and other inorganic compounds of the aforementioned metallic elements; salts of organic acids (e.g., salts of acetic acid, propionic acid, hydrocyanic acid, naphthenic acid and stearic acid), complexes, and other organic compounds of the metallic elements. Ligands for constituting the complexes include OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (e.g., triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

By taking cobalt compounds as example, examples of the metallic compounds include cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt and other complexes, and other divalent or trivalent cobalt compounds. Illustrative vanadium compounds include vanadium hydroxide, vanadium oxide, vanadium chloride, vanadyl chloride, vanadium sulfate, vanadyl sulfate, sodium vanadate, ammonium phosphomolybdovanadate and other inorganic compounds; acetylacetonatovanadium [e.g., $V(acac)_3$], vanadyl acetylacetonato [e.g., VO(acac) 2], vanadyl stearate [$VO(C_{17}H_{35}COO)_2$], vanadyl isopropoxide [$VO(OCH(CE_3)_2)_3$], and other organic vanadium compounds (including complexes) each having a valence of 2 to 5. Examples of compounds of the other metallic elements include compounds corresponding to the above-mentioned cobalt or vanadium compounds. Among them, vanadium compounds are typically preferred as the metallic compounds.

The proportion of the metallic compound is, for example, from about 0.0001 to about 0.7 mole, preferably from about 0.001 to about 0.5 mole, and more preferably from about 0.0015 to about 0.1 mole relative to 1 mole of the substrate.

The metallic compound is often used in a proportion of from about 0.0015 to about 0.05 mole relative to 1 mole of the substrate.

To improve the rate and/or selectivity of the reaction, a promoter (co-catalyst) can be used in combination with the metallic compound, according to necessity, in the process of the present invention. Such promoters include, but are not limited to, organic salts each comprising a polyatomic cation or a polyatomic anion and its counter ion, which polyatomic cation or anion contains a Group 15 or Group 16 element of the Periodic Table of Elements having at least one organic group bonded thereto. Each of these promoters can be used alone or in combination.

In the organic salts, the Group 15 elements of the Periodic Table of Elements include N, P, As, Sb and Bi. The Group 16 elements of the Periodic Table of Elements include, for example, O, S, Se and Te. Preferred elements are N, P, As, Sb and S, of which N, P and S are typically preferred.

Organic groups to be bonded to the atoms of the elements include, for example, hydrocarbon groups which may have a substituent, and substituted oxy groups. The hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having from about 1 to about 30 carbon atoms (preferably from about 1 to about 20 carbon atoms); cyclopentyl, cyclohexyl, and other alicyclic hydrocarbon groups each having from about 3 to about 8 carbon atoms; and phenyl, naphthyl, and other aromatic hydrocarbon groups each having from about 6 to about 14 carbon atoms. Substituents which the hydrocarbon groups may have include, but are not limited to, halogen atoms, oxo group, hydroxyl group, substituted oxy groups (e.g., alkoxy groups, aryloxy groups and acyloxy groups), carboxyl group, substituted oxycarbonyl groups, substituted or unsubstituted carbamoyl groups, cyano group, nitro group, substituted or unsubstituted amino groups, alkyl groups (e.g., methyl, ethyl, and other $C_1$–$C_4$ alkyl groups), cycloalkyl groups, aryl groups (e.g., phenyl and naphthyl groups), and heterocyclic groups. The preferred hydrocarbon groups include, for example, alkyl groups each having from about 1 to about 30 carbon atoms, and aromatic hydrocarbon groups (especially, phenyl or naphthyl group) each having from about 6 to about 14 carbon atoms. The aforementioned substituted oxy groups include, but are not limited to, alkoxy groups, aryloxy groups and aralkyloxy groups.

Typical examples of the organic salts include organic ammonium salts, organic phosphonium salts, organic sulfonium salts, and other organic onium salts. Examples of the organic ammonium salts include tetramethylammonium chloride, tetraethylammonium chloride, tetrabutylammonium chloride, tetrahexylammonium chloride, trioctylmethylammonium chloride, triethylphenylammonium chloride, tributyl(hexadecyl)ammonium chloride, di(octadecyl) dimethylammonium chloride, and other quaternary ammonium chlorides, and corresponding quaternary ammonium bromides, and other quaternary ammonium salts each having four hydrocarbon groups bonded to its nitrogen atom; dimethylpiperidinium chloride, hexadecylpyridinium chloride, methylquinolinium chloride, and other cyclic quaternary ammonium salts. Examples of the organic phosphonium salts include tetramethylphosphonium chloride, tetrabutylphosphonium chloride, tributyl(hexadecyl) phosphonium chloride, triethylphenylphosphonium chloride, and other quaternary phosphonium chlorides, and corresponding quaternary phosphonium bromides, and other quaternary phosphonium salts each having four hydrocarbon groups bonded to its phosphorus atom. Examples of the organic sulfonium salts include triethylsulfonium iodide, ethyldiphenylsulfonium iodide, and other sulfonium salts each having three hydrocarbon groups bonded to its sulfur atom.

The organic salts also include methanesulfonates, ethanesulfonates, octanesulfonates, dodecanesulfonates, and other alkyl-sulfonates (e.g., $C_6$–$C_{18}$ alkylsulfonates); benzenesulfonates, p-toluenesulfonates, naphthalenesulfonates, decylbenzenesulfonates, dodecylbenzenesulfonates, and other aryl-sulfonates which may be substituted with an alkyl group (e.g., $C_6$–$C_{18}$) alkyl-arylsulfonates); sulfonic acid type ion exchange resins (ion exchangers); and phosphonic acid type ion exchange resins (ion exchangers).

The amount of the organic salt is, for example, from about 0.0001 to about 0.7 mole, preferably from about 0.001 to about 0.5 mole, more preferably from about 0.002 to about 0.1 mole, and often from about 0.005 to about 0.05 mole relative to 1 mole of the substrate.

In the process of the present invention, the presence of a peroxide such as t-butyl hydroperoxide (TBHP) in a reaction system can enhance or promote the reaction and thereby significantly increases the yield of a target compound. The amount of the peroxide is, for example, from about 0.0001 to about 0.2 mole, preferably from about 0.001 to about 0.1 mole, and more preferably from about 0.003 to about 0.05 mole relative to 1 mole of the substrate.

[Reaction]

The reaction can be performed in the presence of, or in the absence of, a solvent. Such solvents include, but are not limited to, benzene and other aromatic hydrocarbons; dichloromethane, chloroform, dichloroethane, dichlorobenzene, and other halogenated hydrocarbons; t-butanol, t-amyl alcohol, and other alcohols; acetonitrile, benzonitrile, and other nitriles; acetic acid, propionic acid, an5d other organic acids; formamide, acetamide, dimethylformamide (DMF), dimethylacetamide, and other amides; and mixtures of these solvents.

The process of the present invention is distinguishable from conventional equivalents in that sulfonation and other reactions can smoothly proceed even under relatively mild conditions. In addition, the reaction does not require light irradiation and can smoothly proceed even under dark conditions. A reaction temperature can be selected within the range from about 0° C. to about 150° C., preferably from about 10° C. to about 125° C., and more preferably from about 15° C. to about 100° C. The reaction can be performed either under atmospheric pressures or under a pressure (under a load), in any of a batch system, a semi-batch system and a continuous system.

The reaction can yield an organic sulfur acid such as a sulfonic acid or sulfinic acid corresponding to the substrate. For example, the combination use of sulfur dioxide and oxygen can produce sulfonic acid in a good yield. The formed organic sulfur acid can be converted into a corresponding salt thereof (e.g., a thiuronium salt) according to conventional techniques. For example, the salt can be obtained by reacting the organic sulfur acid with an alkali metal hydroxide, alkali metal carbonate, alkali metal hydrogencarbonate, alkaline earth metal hydroxide, alkaline earth metal carbonate, amine, thiourea, or isothiourea in an appropriate solvent such as water.

After the completion of the reaction, reaction products can be easily separated and purified in a conventional manner such as filtration, concentration, distillation, extraction, crystallization, recrystallization, column chromatography and other separation and purification means, or any combination of these means.

Important compounds that can be obtained by the process of the present invention include, for example,
1-adamantanesulfonic acid;
3,5-dimethyl-1-adamantanesulfonic acid,
3-carboxy-1-adamantanesulfonic acid,
3-chloro-1-adamantanesulfonic acid,
4-oxo-1-adamantanesulfonic acid, and other 1-adamantanesulfonic acid derivatives each having a substituent such as methyl group, carboxyl group, halogen atom or oxo group on an adamantane ring; cyclohexanesulfonic acid, cyclooctanesulfonic acid, and other cycloalkanesulfonic acids; octanesulfonic acid, 2,5-dimethylhexanesulfonic acid, and other alkanesulfonic acids. These compounds are useful as raw materials for pharmaceuticals, agrochemicals and dyes and as detergents, polymer materials, light-activatable acid generators or materials therefor.

INDUSTRIAL APPLICABILITY

The process of the present invention can efficiently produce an organic sulfur acid or a salt thereof by catalysis of a small amount of an easily available catalyst under mild conditions, without the use of the imide compounds of Formula (1) such as N-hydroxyphthalimide. Additionally, the process can directly and efficiently yield a corresponding organic sulfur acid or a salt thereof from a non-aromatic hydrocarbon.

EXAMPLES

The present invention will now be illustrated in more detail with reference to several examples below, which are not intended to limit the scope of the invention. In the examples, a benzylthiuronium salt of a produced sulfonic acid was obtained by extracting a reaction mixture with water, neutralizing the extract with an aqueous sodium hydroxide solution, adjusting the resulting solution with hydrochloric acid to weak acidity, adding an excess of an aqueous benzylisothiourea hydrochloride to the resulting solution, and recovering the precipitated solid by filtration.

Example 1

A mixture of 2 mmol of adamantane, 0.01 mmol of acetylacetonatovanadium [V(acac)$_3$] and 10 ml of acetic acid was stirred at 40° C. in an atmosphere of sulfur dioxide (SO$_2$) (0.5 atm=50.5 kPa) and oxygen (0.5 atm=50.5 kPa) for 2 hours. The resulting reaction mixture was analyzed by high performance liquid chromatography to find that 1-adamantanesulfonic acid was produced in a yield of 47% (selectivity: 94%) with a conversion from adamantane of 50%.

Example 2

The procedure of Example 1 was repeated, except that 0.01 mmol of vanadyl acetylacetonato [(VO(acac)$_2$] was used instead of acetylacetonatovanadium [V(acac)$_3$], and thereby yielded 1-adamantanesulfonic acid in a yield of 42% (selectivity: 98%) with a conversion from adamantane of 43%.

Example 3

The procedure of Example 1 was repeated, except that 0.01 mmol of vanadyl stearate [VO(C$_{17}$H$_{35}$COO)$_2$] was used instead of acetylacetonatovanadium [V(acac)$_3$], and thereby yielded 1-adamantanesulfonic acid in a yield of 49% (selectivity: 88%) with a conversion from adamantane of 56%.

Example 4

The procedure of Example 1 was repeated, except that 0.01 mmol of vanadyl isopropoxide [VO(OCH(CH$_3$)$_2$)$_3$] was used instead of acetylacetonatovanadium [V(acac)$_3$], and thereby yielded 1-adamantanesulfonic acid in a yield of 29% (selectivity: 78%) with a conversion from adamantane of 37%.

Example 5

The procedure of Example 1 was repeated, except that 0.01 mmol of vanadyl chloride (VOCl$_3$) was used instead of acetylacetonatovanadium [V(acac)$_3$], and thereby yielded 1-adamantanesulfonic acid in a yield of 33% (selectivity: 85%) with a conversion from adamantane of 39%.

Example 6

The procedure of Example 1 was repeated, except that 0.01 mmol of ammonium phosphomolybdovanadate was used instead of acetylacetonatovanadium [V(acac)$_3$], and thereby yielded 1-adamantanesulfonic acid in a yield of 15% (selectivity: 60%) with a conversion from adamantane of 25%.

Example 7

A mixture of 2 mmol of 1,3-dimethyladamantane, 0.01 mmol of vanadyl acetylacetonato [VO(acac)$_2$] and 10 ml of acetic acid was stirred at 40° C. in an atmosphere of sulfur dioxide (SO$_2$) (0.5 atm =50.5 kPa) and oxygen (0.5 atm= 50.5 kPa) for 5 hours. The resulting reaction mixture was analyzed by high performance liquid chromatography to find that 3,5-dimethyl-1-adamantanesulfonic acid was produced in a yield of 50% with a conversion from 1,3-dimethyladamantane of 54%.

[Spectral Data of 3,5-Dimethyl-1-adamantanesulfonic Acid]

$^{13}$C-NMR (CD$_3$OD) δ: 59.8, 52.4, 44.4, 44.3, 37.2, 33.1, 32.3

$^1$H-NMR (CD$_3$OD) δ: 5.59 (br, —SO$_3$H), 2.16–2.10 (m, 1H), 1.85–1.83 (m, 2H), 1.70–1.50 (m, 4H), 1.50–1.30 (m, 4H), 1.30–1.10 (m, 2H), 0.83 (s, 6H)

[Spectral Data of Benzylthiuronium Salt of 3,5-Dimethyl-1-adamantanesulfonic Acid]

$^{13}$C-NMR (CD$_3$OD) δ: 135.9, 130.9, 130.8, 130.2, 59.5, 52.4, 44.8, 44.5, 37.4, 37.0, 33.2, 31.7

$^1$H-NMR (CD$_3$OD) δ: 7.43–7.32 (m, 5H), 4.85 (s, 4H), 4.43 (s, 2H), 2.15–2.12 (m, 1H), 1.85–1.84 (m, 2H), 1.69–1.58 (m, 4H), 1.34 (s, 4H), 1.13 (m, 2H), 0.85 (m, 6H)

FT-IR (cm$^{-1}$): 3323, 3133, 2942, 2900, 1455, 1388, 1088, 1041, 708, 692

Example 8

The procedure of Example 7 was repeated, except that the reaction was performed at 25° C. for 24 hours, and thereby yielded 3,5-dimethyl-1-adamantanesulfonic acid in a yield of 45% with a conversion from 1,3-dimethyladamantane of 50%.

Example 9

A mixture of 2 mmol of 1-adamantanecarboxylic acid, 0.01 mmol of vanadyl acetylacetonato [VO(acac) 2] and 10 ml of acetic acid was stirred at 40° C. in an atmosphere of sulfur dioxide ($SO_2$) (0.5 atm=50.5 kPa) and oxygen (0.5 atm=50.5 kPa) for 5 hours. The resulting reaction mixture was analyzed by high performance liquid chromatography to find that 3-carboxy-1-adamantanesulfonic acid was produced in a yield of 65% with a conversion from 1-adamantanecarboxylic acid of 70%.

[Spectral Data of 3-Carboxy-1-adamantanesulfonic Acid]

$^{13}$C-NMR ($CD_3OD$) δ: 180.0, 58.8, 42.8, 39.6, 39.2, 38.8, 37.2, 36.2, 30.3

$^1$H-NMR ($CD_3OD$) δ: 6.24 (br, —$SO_3H$), 2.15–1.60 (m, 14H)

[Spectral Data of Benzylthiuronium Salt (.$H_2O$) of 3-Carboxy-1-adamantanesulfonic Acid]

$^{13}$C-NMR ($CD_3OD$) δ: 180.6, 135.1, 130.1, 130.0, 129.4, 56.9, 42.4, 39.4, 39.0, 37.1, 36.3, 36.2, 29.7

$^1$H-NMR ($CD_3OD$) δ: 7.43–7.32 (m, 5H), 4.89 (s, 4H), 4.43 (s, 2H), 2.14–1.67 (m, 14H)

FT-IR ($cm^{-1}$): 3061, 2819, 2664, 1693, 1460, 1202, 1161, 1036, 701, 625

Example 10

A mixture of 2 mmol of 1-chloroadamantane, 0.01 mmol of vanadyl acetylacetonato [$VO(acac)_2$] and 10 ml of acetic acid was stirred at 40° C. in an atmosphere of sulfur dioxide ($SO_2$) (0.5 atm=50.5 kPa) and oxygen (0.5 atm=50.5 kPa) for 5 hours. The resulting reaction mixture was analyzed by high performance liquid chromatography to find that 3-chloro-1-adamantanesulfonic acid was produced in a yield of 53% with a conversion from 1-chloroadamantane of 56%.

[Spectral Data of 3-Chloro-1-adamantanesulfonic Acid]

$^{13}$C-NMR ($CD_3OD$) δ: 68.2, 60.0, 47.3, 36.2, 35.2, 32.9

$^1$H-NMR ($CD_3OD$) δ: 5.58 (br, —$SO_3H$), 2.33–1.60 (m, 14H)

[Spectral Data of Benzylthiuronium Salt of 3-Chloro-1-adamantanesulfonic Acid]

$^{13}$C-NMR ($CD_3OD$) δ: 135.1, 130.2, 130.1, 129.5, 68.3, 59.7, 47.7, 42.6, 36.4, 36.2, 35.4, 32.7

$^1$H-NMR ($CD_3OD$) δ: 7.40–7.34 (m, 5H), 4.85 (s, 4H), 4.43 (s, 2H), 2.33–1.63 (m, 14H)

FT-IR ($cm^{-1}$) 3088, 2910, 1666, 1495, 1334, 1174, 1013, 714, 629

Example 11

The procedure of Example 10 was repeated, except that the reaction was performed in an atmosphere of sulfur dioxide ($SO_2$) (0.67 atm=67.7 kPa) and oxygen (0.33 atm=33.3 kPa), and thereby yielded 3-chloro-1-adamantanesulfonic acid in a yield of 75% with a conversion from 1-chloroadamantane of 82%.

Example 12

A mixture of 2 mmol of 2-oxoadamantane, 0.01 mmol of vanadyl acetylacetonato [$VO(acac)_2$] and 10 ml of acetic acid was stirred at 40° C. in an atmosphere of sulfur dioxide ($SO_2$) (0.5 atm=50.5 kPa) and oxygen (0.5 atm=50.5 kPa) for 30 hours. The resulting reaction mixture was analyzed by high performance liquid chromatography to find that 4-oxo-1-adamantanesulfonic acid was produced in a yield of 20% with a conversion from 2-oxoadamantane of 26%.

[Spectral Data of 4-Oxo-1-adamantanesulfonic Acid]

$^{13}$C-NMR ($CD_3OD$) δ: 106.6, 57.6, 37.4, 34.9, 34.8, 33.3, 28.9, 28.3

$^1$H-NMR ($CD_3OD$) δ: 6.95 (br, —$SO_3H$), 2.50–1.40 (m, 13H)

Example 13

A mixture of 2 mmol of cyclohexane, 0.01 mmol of vanadyl acetylacetonato [$VO(acac)_2$] and 10 ml of acetic acid was stirred at 40° C. in an atmosphere of sulfur dioxide ($SO_2$) (0.5 atm=50.5 kPa) and oxygen (0.5 atm=50.5 kPa) for 24 hours. The resulting reaction mixture was analyzed by high performance liquid chromatography to find that cyclohexanesulfonic acid was produced in a yield of 36% with a conversion from cyclohexane of 46%.

[Spectral Data of Benzylthiuronium Salt (.$H_2O$) of Cyclohexanesulfonic Acid]

$^{13}$C-NMR ($CD_3OD$) δ: 135.9, 130.9, 130.8, 130.2, 61.4, 37.0, 29.5, 27.5, 27.4

$^1$H-NMR ($CD_3OD$) δ: 7.44–7.30 (m, 5H), 4.88 (s, 4H), 4.43 (s, 2H), 2.65–2.55 (m, 1H), 2.18–2.14 (m, 2H), 1.84–1.14 (m, 8H)

FT-IR ($cm^{-1}$) 3087, 2838, 1669, 1451, 1225, 1044, 698, 526

Example 14

A mixture of 2 mmol of cyclooctane, 0.01 mmol of vanadyl acetylacetonato [$VO(acac)_2$] and 10 ml of acetic acid was stirred at 40° C. in an atmosphere of sulfur dioxide ($SO_2$) (0.5 atm=50.5 kPa) and oxygen (0.5 atm=50.5 kPa) for 5 hours. The resulting reaction mixture was analyzed by high performance liquid chromatography to find that cyclooctanesulfonic acid was produced in a yield of 45% with a conversion from cyclooctane of 53%.

[Spectral Data of Cyclooctanesulfonic Acid]

$_{13}$C-NMR ($CD_3OD$) δ: 61.9, 28.8, 28.4, 28.3, 37.6

$^1$H-NMR ($CD_3OD$) δ: 7.45 (br, —$SO_3H$), 3.00–2.70 (m, 1H), 2.40–1.25 (m, 14H)

[Spectral Data of Benzylthiuronium Salt of Cyclooctanesulfonic Acid]

$^{13}$C-NMR ($CD_3OD$) δ: 136.0, 130.9, 130.8, 130.3, 62.0, 37.1, 30.0, 28.4, 28.3, 27.5

$^1$H-NMR ($CD_3OD$) δ: 7.43–7.32 (m, 5H), 4.85 (s, 4H), 4.43 (s, 2H), 2.84–2.80 (m, 1H), 2.21–2.17 (m, 2H), 1.73–1.54 (m, 12H)

FT-IR ($cm^{-1}$): 3094, 2927, 1670, 1454, 1188, 1040, 761, 611

Example 15

The procedure of Example 14 was repeated, except that the reaction was performed for 24 hours, and thereby yielded cyclooctanesulfonic acid in a yield of 62% with a conversion from cyclooctane of 68%.

Example 16

A mixture of 2 mmol of 2,5-dimethylhexane, 0.01 mmol of vanadyl acetylacetonato [$VO(acac)_2$] and 10 ml of acetic acid was stirred at 60° C. in an atmosphere of sulfur dioxide ($SO_2$) (0.5 atm=50.5 kPa) and oxygen (0.5 atm=50.5 kPa) for 24 hours. The resulting reaction mixture was analyzed by high performance liquid chromatography to find that 2,5-dimethylhexanesulfonic acid was produced in a yield of 6% with a conversion from 2,5-dimethylhexane of 18%.

Example 17

A mixture of 2 mmol of n-octane, 0.01 mmol of vanadyl acetylacetonato [$VO(acac)_2$] and 10 ml of acetic acid was stirred at 60° C. in an atmosphere of sulfur dioxide ($SO_2$) (0.67 atm=67.7 kPa) and oxygen (0.33 atm=33.3 kPa) for 15 hours. The resulting reaction mixture was analyzed by high performance liquid chromatography to find that octanesulfonic acid was produced with a conversion from n-octane of 64%.

[Spectral Data of Octanesulfonic Acid]

$^{13}$C-NMR (CD$_3$OD) δ: 56.6, 54.0, 53.1, 39.3, 37.3, 29.7, 18.7, 15.5, 13.9, 13.7, 13.2, 11.4, 9.1

What is claimed is:

1. A process for producing an organic sulfur acid or a salt thereof, the process comprising the step of allowing an organic substrate to react with a sulfur oxide in the presence of a metallic compound catalyst selected from the group consisting of inorganic vanadium compounds and vanadium complexes and in the absence of N-hydroxy and N-oxo cyclic imide compounds to thereby yield a corresponding organic sulfur acid or a salt thereof.

2. The process for producing an organic sulfur acid or a salt thereof according to claim 1, wherein sulfur dioxide is used as the sulfur oxide.

3. The process for producing an organic sulfur acid or a salt thereof according to claim 1, wherein the organic substrate is one selected from (a) homocyclic or heterocyclic compounds each having a methylene group; (b) compounds each having a methine carbon atom; (c) compounds each having a methyl group or a methylene group at the adjacent position to an unsaturated bond; (d) non-aromatic heterocyclic compounds each having a carbon-hydrogen bond at the adjacent position to a hetero atom; and (e) straight-chain alkanes.

4. The process of claim 1, wherein the inorganic vanadium compound is vanadium hydroxide, vanadium oxide, vanadium chloride, vanadyl chloride, vanadium sulfate, vanadyl sulfate, sodium vanadate, or ammonium phosphomolybdovanadate.

5. The process of claim 1, wherein the vanadium complex is acetylacetonatovanadium, vanadyl acetylacetonato, or vanadyl isopropoxide.

* * * * *